United States Patent [19]
Cox

[11] Patent Number: 5,657,749
[45] Date of Patent: Aug. 19, 1997

[54] INHALATION DEVICE

[75] Inventor: Peter Erich Cox, Cherry Hinton, Great Britain

[73] Assignee: Glaxo Group Limited, London, England

[21] Appl. No.: 392,741

[22] PCT Filed: Sep. 9, 1993

[86] PCT No.: PCT/EP93/02439

§ 371 Date: Mar. 7, 1995

§ 102(e) Date: Mar. 7, 1995

[87] PCT Pub. No.: WO94/06497

PCT Pub. Date: Mar. 31, 1994

[30] Foreign Application Priority Data

Sep. 11, 1992 [GB] United Kingdom ............ 9219282
Jun. 3, 1993 [GB] United Kingdom ............ 9311442

[51] Int. Cl.[6] ........................................... A61M 15/00
[52] U.S. Cl. ........................... 128/203.15; 128/203.23
[58] Field of Search ............... 128/203.15, 203.23, 128/203.21, 203.12

[56] References Cited

FOREIGN PATENT DOCUMENTS 0 525 720 A1 2/1993 European Pat. Off. .
0 528 764 A1 2/1993 European Pat. Off. .
8121383 5/1983 France .................. 128/203.15

Primary Examiner—Edgar S. Burr
Assistant Examiner—Daniel J. Colilla
Attorney, Agent, or Firm—Bacon & Thomas

[57] ABSTRACT

The invention relates to an inhalation device by which powdered material can be inhaled. A plurality of powder containers, each having a powder containing depression therein, may be individually fed to a use station which cooperates with an inhalation means. The inhalation means includes an outlet communicating with the open container by a passage, which passage has a wall means which cooperates with the powder containing depression to define a venturi.

13 Claims, 9 Drawing Sheets

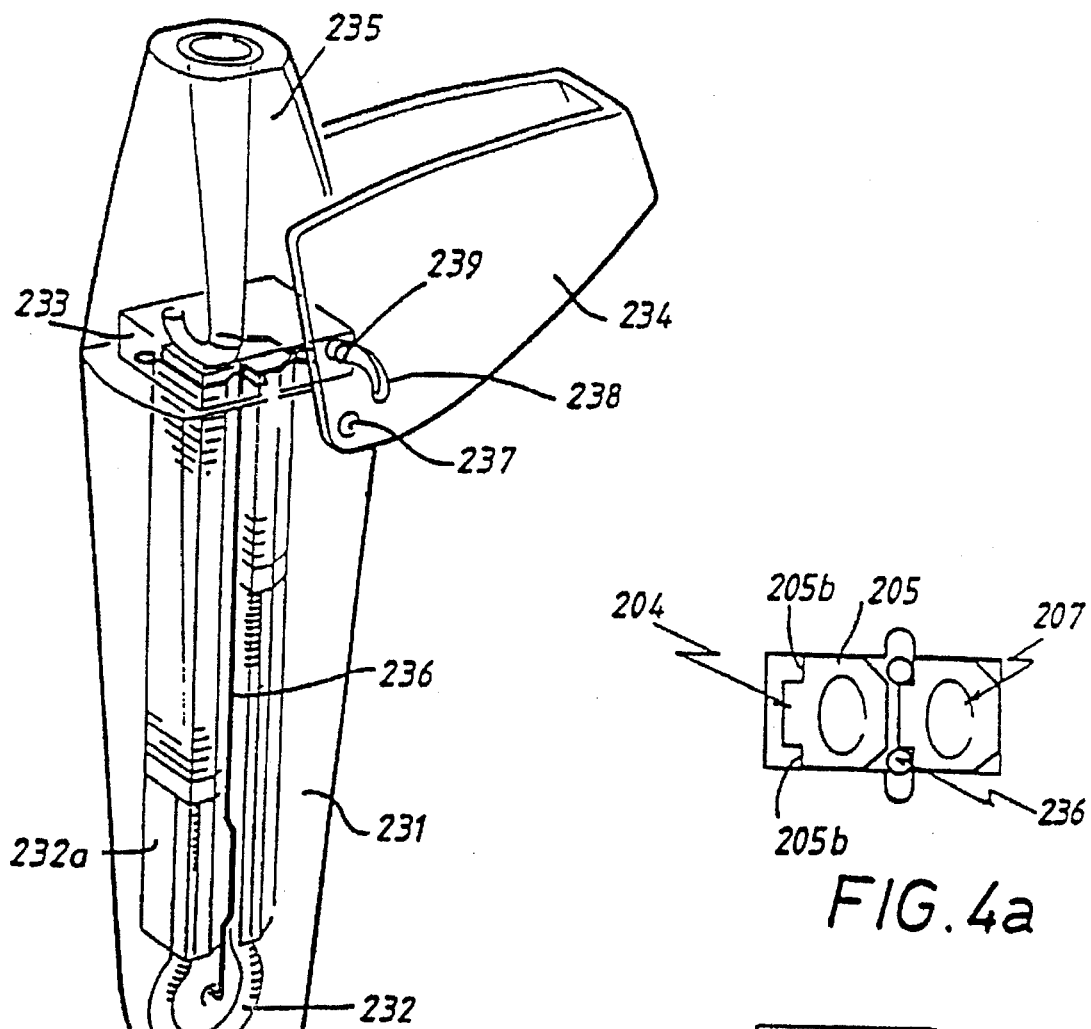
FIG. 4
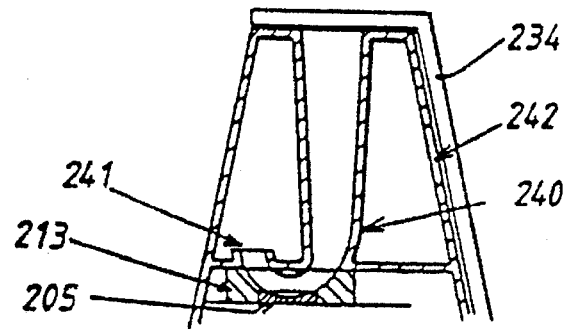
FIG. 4a
FIG. 4b
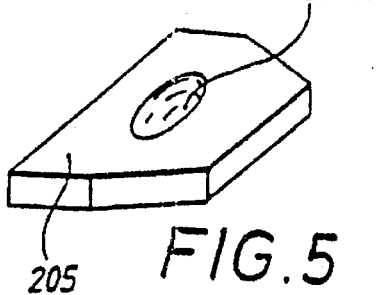
FIG. 5

5,657,749

INHALATION DEVICE

BACKGROUND OF THE INVENTION

This invention relates to an inhalation device for use in the inhalation of material in powder form. More particularly, it relates to a device by means of which medicament in powder form can be inhaled, and it is so described below.

SUMMARY OF THE INVENTION

According to the present invention there is provided an inhalation device by means of which material in powder form can be inhaled, comprising means holding a powder container having a powder-containing depression therein at a use station, and inhalation means for enabling the powder to be inhaled from a container at the use station, said inhalation means comprising an outlet communicating with the open container by a passage, said passage comprising wall means which cooperate with the said depression to define a venturi.

The use of a venturi is advantageous in that it provides for rapid and substantially complete emptying of the container.

The invention further provides for the use of such an inhalation means in an inhalation device by means of which material in powder form can be inhaled, comprising means for holding a stack of unused powder containers and storage means for receiving each used container from the use station after the powder has been inhaled therefrom and collecting the containers therein.

The invention can also be used with other types of inhalation means such as in an inhalation device as described in GB-A-2242134 in which at least one powder container is defined between two members peelably secured to one another, the device comprising means defining an opening station for the said at least one container, and means for peeling the members apart at the opening station to open the container.

The invention additionally can be used with an inhalation device as described in WO 92/00771 in which there is provided a storage chamber for the powder to be inhaled and a metering member which is intended to provide at least one dispensing cup defining the at least one powder container, the said metering member being moveable between a first position in which a container is presented to the storage chamber to receive a dose of the powder to be inhaled and a second position defined by the use station.

BRIEF DESCRIPTION OF THE DRAWINGS

The invention is further described below with reference to the accompanying drawings, in which:

FIG. 4 is a perspective view of a device embodying the principles of FIGS. 1 to 3;

FIG. 4a is a view from above showing part of the device of FIG. 4;

FIG. 4b is a vertical section through part of the device of FIG. 4, showing in more detail the design of the mouthpiece thereof;

FIG. 5 shows a single powder container;

DETAILED DESCRIPTION OF THE PREFERRED EMBODIMENTS

Figure 1:
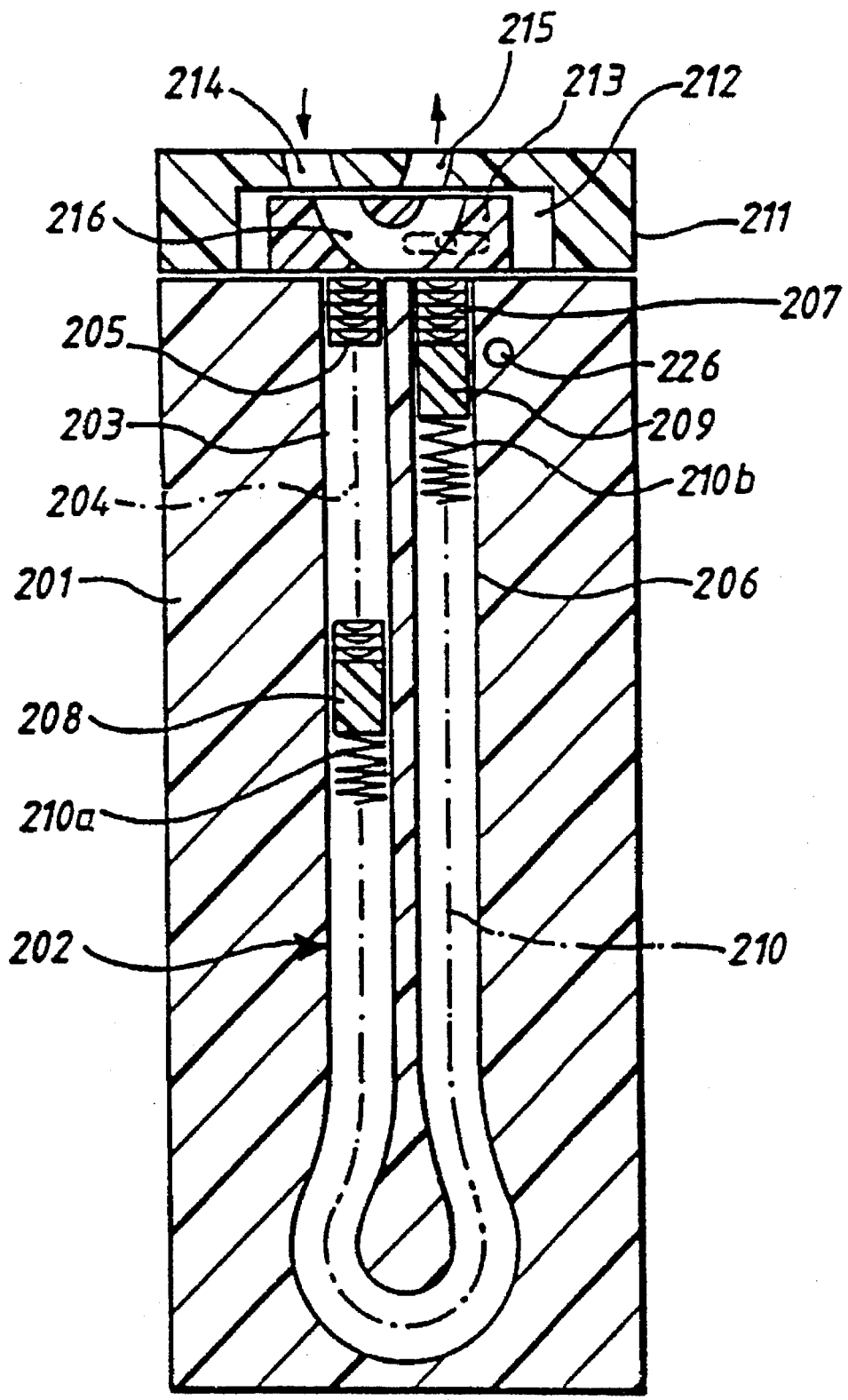
FIG. 1 is a side view, in section, showing diagrammatically a first embodiment of the present invention.

In the embodiment shown in FIGS. 1 to 4, a body 201 is provided within which is formed a generally U-shaped passage 202. This passage comprises a first straight portion 203 which contains a stack 204 of unused, i.e. powder-containing, powder containers 205, and a second straight portion 206 which contains a stack 207 of used, i.e. empty, powder containers. At the lower end of the stack 204 is a piston 208, and at the lower end of the stack 207 is a piston 209. A coil spring 210 is located, in a state of compression, within the U-shaped passage 202, with one end of the spring bearing against the piston 208 and the other end of the spring bearing against the piston 209. The spring 210 has end portions 210a and 210b in which adjacent turns of the spring are spaced somewhat from one another, whilst over the rest of the length of the spring the coils are located tightly against one another. The effect of this is that the spring 210 provides a flexible member of substantially constant length, with a substantially constant spring force being generated only by the end portions 210a and 210b.

It should be mentioned at this point that other forms of spring can be used instead. Thus, for example, a simple compression spring, with the turns equally spaced apart over its whole length, could be used, However, to achieve the same compression stiffness as the spring 210 described, this would need to be made of relatively thick wire, and would therefore be less able to bend in the curved portion of the U-shaped passage. Another possibility is to use a flexible flat strip of metal or a plastics material, with a short compression spring at each end thereof. This has the advantage that the flat strip can be made highly flexible, and can therefore bend round a tighter radius than a conventional circular cross-section spring. However, it has the disadvantages that it involves additional components, and, in the case of a plastics strip, the material may creep with time. Yet another possibility is to use a flat strip formed into integral 'Z' springs at each end. This provides a highly flexible spring, whilst avoiding the need for more than one component, although the spring needs to be carefully designed to achieve an adequate load. Metal is preferred as a material for the strip, since a plastics strip would be liable to creep.

A cover 211 is secured to the top of the body 201, and has a recess 212, which is rectangular both in vertical section and plan view on the underside thereof. A slider 213 is slidably mounted in the recess 212. The cover 211 has an air inlet passage 214 and an outlet passage 215 for air and powder. In practice, the passage 215 is connected to a mouthpiece or nosepiece for inhalation, though this is not shown in FIG. 1. The slider 213 has a passage 216 which opens into the lower face of the slider 213. When the slider 213 is in its left hand position (it is shown in an intermediate position in FIG. 1) the opening in the passage 216 communicates with the upper end of the stack 204 and the ends of the passage 216 communicate respectively with the passages 214 and 215. Thus, when the slider 213 is in the left hand position, inhalation by the user through the mouthpiece or nosepiece attached to passage 215 causes air to flow in through passage 214 and thence through passage 216, entraining powder from the topmost of the containers 205 in the stack 204, and thence, with the powder entrained therein, out through the passage 215. Each of the containers 205 has a depression in its upper surface to hold the powder, and the shape of this depression is preferably such that it forms a smooth continuation with the adjacent wall of the passage 216, thereby to improve the efficiency with which powder is scoured from the depression by the air flow. The combination of the passages 214, 215 and 216, and the depression in the container 205 forms a venturi, as can be seen in FIG. 1.

The slider 213 operates to transfer each powder container, as it is used, from the top of stack 204 to the top of stack 207. The slider can be seen in more detail in FIGS. 2 and 3. It will be seen there that it has a recess 217 on the underside thereof, the recess being defined by a shoulder 218 at one end and a ramp 219 at the other end. As the slider 213 moves from left to right, (as viewed in all of FIGS. 1 to 3), the shoulder 218 engages the left hand edge of the container 205 which is at the top of the stack 204. The slider moves this container onto the top of the existing stack 207 of used containers. The leading lower edge portion 220 of the slider 213 stays in contact with the top of the existing stack 207 until after the leading edge of the new used container 205 is over the edge of the stack 207. This ensures that the new used container is free to assume its desired position on the top of the existing stack.

When the slider 213 is then moved leftwards, the stack 207 is progressively compressed as the right hand edge of the top container in the stack is engaged by the ramp 219, until the leading edge portion 220 is over the top of the stack 207. During this leftward motion of the slider 213 the top container in the stack 207 is prevented from moving leftwardly by a non-return catch which is provided by a pair of pins 221. The pins pass through apertures 223 in the cover 211 and are biased towards one another, and in FIG. 2 this is shown as being achieved by flexible resilient members 222. However, any suitable alternative biasing means could be used instead. The inner ends of the pins 221 are bevelled so that although they prevent the slider carrying containers from right to left they do not prevent the slider carrying containers from left to right.

One of the containers 205, with its depression 205a, is shown on a larger scale in FIG. 5, and it can be seen to be generally rectangular in plan, but with two opposite bevelled edges (not labeled). It will be appreciated that these are convenient from the point of view of the operation of the non-return catch in FIG. 2.

Figure 3:
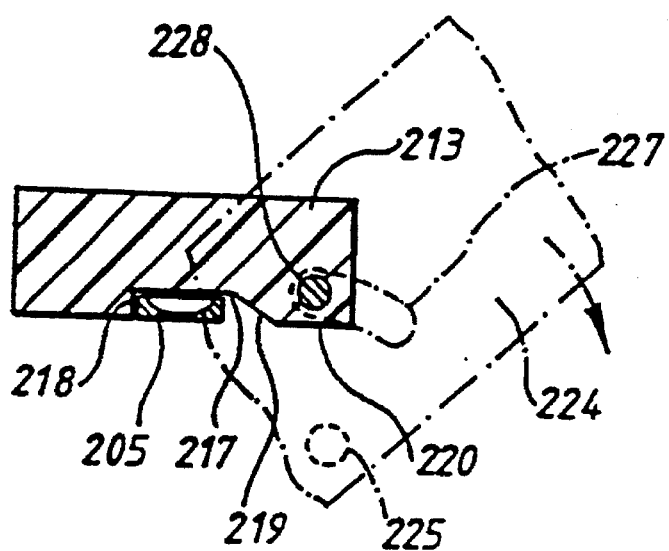
FIG. 3 is a sectional view generally taken along line III—III in FIG. 2, but showing only slider and container component of FIG. 2.

The slider 213 may be moved back and forth, for example, by a lever 224, part of which is indicated in broken lines in FIG. 3. The lever is pivotally mounted on the body 201 by a shaft 225, which passes through a bore 226 indicated in FIG. 1. The lever itself is not shown in FIG. 1. The lever has an arcuate slot 227 which receives the end of a pin 228 which is fixedly secured in the slider 213. The lever 224 is shown moving clockwise, so as to carry the pin 228, and hence the slider 213, rightwardly.

The use of a pin and slot provides lost motion between the lever 224 and the slider 213. In an actual inhalation device this lost motion can be used as movement in which a cap closing the device is moved from a closed to an open position. Thus, in practice, the lever 224 could be constituted by the cap itself, with the initial part of the cap opening movement having no effect on the slider 213, and the final part of the cap opening movement serving to bring the last used container 205 from the stack 204 to the stack 207, and thus expose a fresh container at the top of stack 204 for use. An example of this is shown in FIGS. 4, 4a and 4b. This comprises a body 231 with a U-shaped passage 232, a compression spring 232a and a slider 233. The device is closed by a pivotally mounted mouthpiece cap 234 which provides the lever to move the slider 233 aside, against the resilient force of the spring. The cap 234 is pivotally mounted on the body 231 by shafts 237, and has arcuate slots 238 in which pins 239 engage, the pins 239 being attached to the slider.

The device has a mouthpiece 235. The mouthpiece 235 is hollow and has within it a venturi passage 240. The passage 240 has an air inlet 241 which air reaches preferably via an aperture 242 in the mouthpiece. The aperture 242 is sealed when the cap 234 is in its closed position, as illustrated in FIG. 4b. The slider 213 and a container 205 define together part of the wall of the venturi passage.

Figure 2:
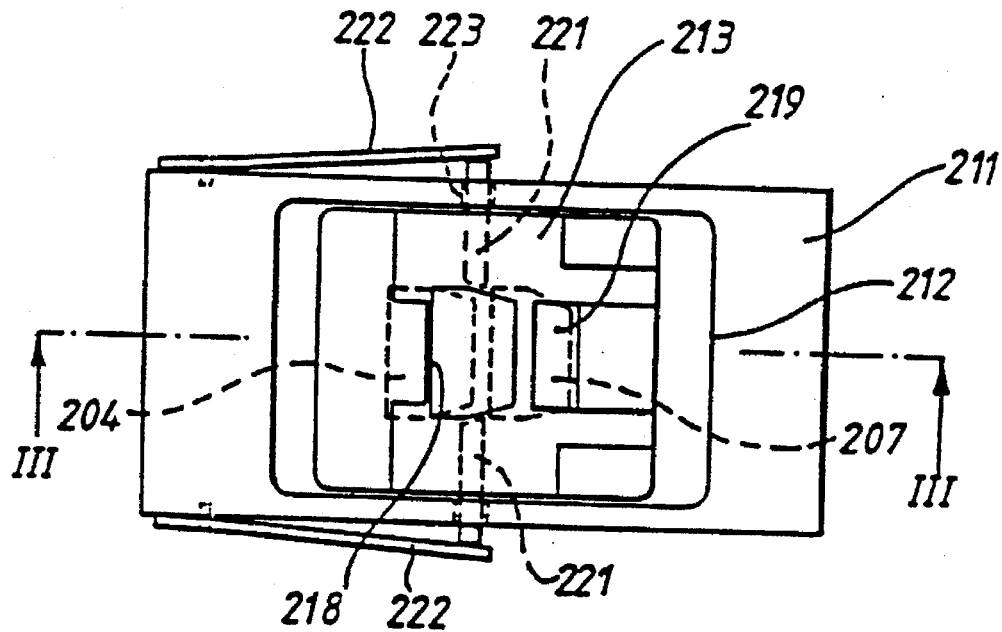
FIG. 2 is an underplan view of the upper portion of the embodiment shown in FIG. 1, on a larger scale.

The principle of operation of the slider is substantially the same as in FIGS. 1 to 3, except that the pins 221 and resilient members 222 are replaced by a single U-shaped spring 236. As shown in FIG. 4a, the containers 205 are modified in that they are provided with cutouts 205b, and the ends of spring 236 engage in the cutouts of the used containers in stack 207. As each container moves from stack 204 to stack 207, it forces the ends of spring 236 apart.

The devices shown in FIGS. 1 to 3 and FIG. 4 employ a linearly moving slider. In an alternative device the slider is moved arcuately by a pivotally mounted member, and this is shown in FIGS. 6a, 6b, 7a, 7b, 8a and 8b.

In the embodiment of FIGS. 6 to 8, the "slider" is constituted by a portion of the mouthpiece adjacent the body within which the stacks of powder containers are held. In these figures the body is denoted by reference 250, the mouthpiece by reference 251, the stack of unused containers by reference 252 and the stack of used containers by reference 253.

Figure 6A:
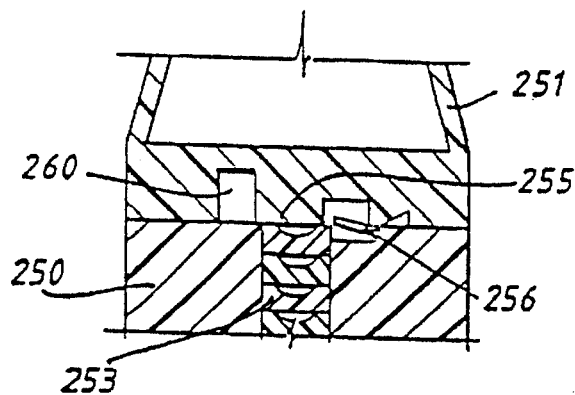
FIGS. 6a and 6b show a body and slider mechanism of part of an embodiment employing a rotary slider, with FIG. 6a being a section on line 6a—6a in FIG. 6b.
Figure 6B:
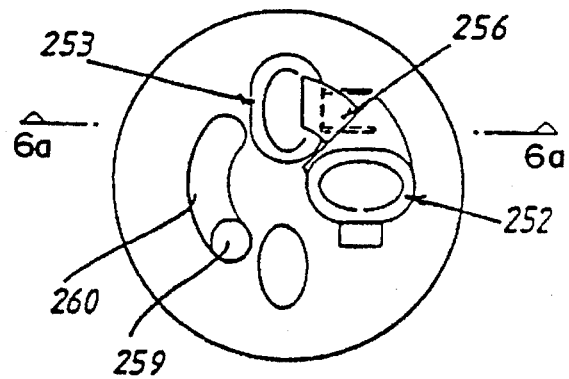
Figure 7A:
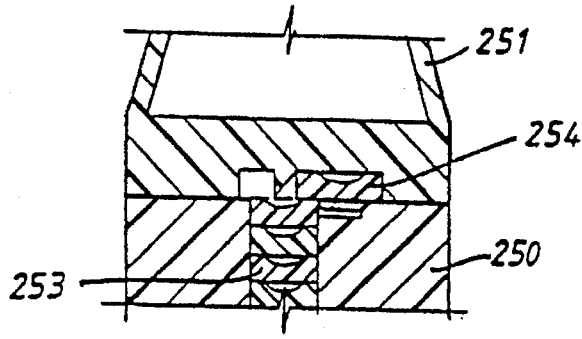
FIGS. 7a and 7b, and 8a and 8b are views corresponding to FIGS. 6a and 6b, with the components in other positions.
Figure 7B:
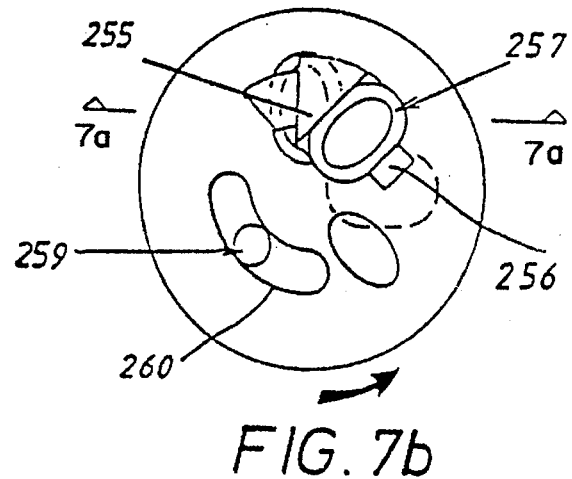
Figure 8A:
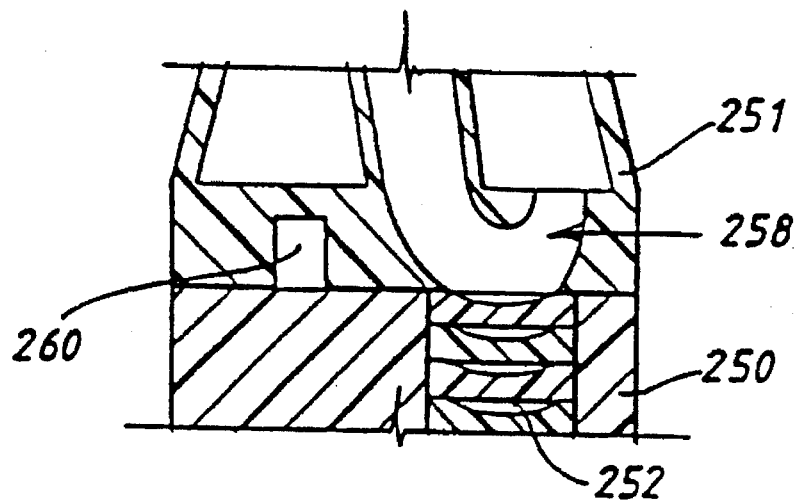
Figure 8B:
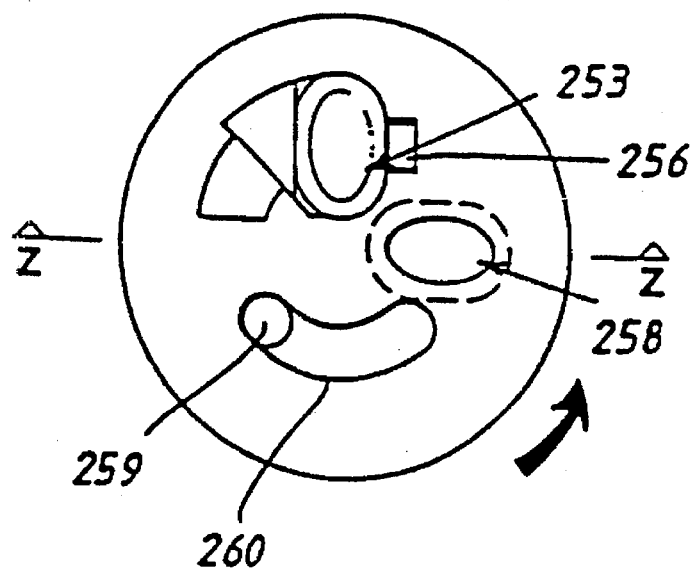

The mouthpiece 251 and body 250 are rotatable relative to one another through an angle of 90° about an axis which is the longitudinal axis of the device, i.e. an axis which is perpendicular to the plane of the paper in FIGS. 6b, 7b and 8b. The description will be given on the basis that the body is fixed and the mouthpiece rotates, but it will be understood that all that matters is the relative rotation between these two components. Rotation is limited to 90° by means of a stud 259 which is formed on the upper surface of the body 250 and which runs in an arcuate track 260 formed in the lower portion of the mouthpiece 251. This 90° rotation correlates with the fact that the stack 252 and the stack 253 are disposed at 90° with respect to one another about the axis of rotation of the mouthpiece. It must be understood, however, that the stacks could be at other angles with respect to one another, in which case the angle of rotation would be correspondingly different.

In the position shown in FIGS. 6a and 6b, the container at the top of the full stack 252 sits in a cutout 254 on the underside of the mouthpiece. This cannot be seen in FIGS. 6a and 6b, but is visible in FIG. 7a. The cup at the top of the empty stack 253 is held down by a portion of an inclined ramp 255, also formed on the lower portion of the mouthpiece 251. The cup at the top of the empty stack 253 is held in line with the rest of the stack by a resilient non-return catch 256 formed on the top of the body 250.

To index the device into a position in which it can be used, the mouthpiece 251 is rotated counter-clockwise with respect to the body 250, as viewed in FIGS. 6b, 7b and 8b. This is indicated by arrows in each of the FIGS. 7b and 8b. At the start of this indexing process, the container at the top of the stack 252 is an empty container, this being the container from which the user last inhaled. As indicated in FIGS. 7a and 7b, this container, denoted there by reference 257, starts to move over the top of the stack 253 of empty containers, holding what was previously the top container of the stack 253 down while the ramp 255 moves away from the stack 253.

When transfer of the container 257 is complete, the catch 256 rises behind that container, as shown in FIG. 8b. The venturi 258 in the mouthpiece is now in position over a full container at the top of the stack 252, and the device is in its primed position, ready for inhalation.

After the user has inhaled the powder from the top container, the mouthpiece is rotated clockwise through 90° to bring the device back to the position shown in FIGS. 6a and 6b. During this clockwise rotation the transferred container 257 is forced down into the stack 253 of empty containers by the ramp 255, and the catch 256 prevents the container 257 being drawn back towards the stack 252. When the 90° clockwise rotation has been completed, the newly emptied container on top of stack 252 snaps up into the cutout 254 in the mouthpiece 251, ready for the next operation.

FIGS. 9, 9a, 10a, 10b and 11 show a further embodiment in which, like the embodiments of FIGS. 1 to 8, there is a U-shaped passage containing a stack of unused containers and a stack of used containers. As in the case of the embodiments of FIGS. 1 to 4, containers are shifted from the top of one stack to the top of the other stack by a translational movement.

The device comprises a body 300 in which there is an outlet spout in the form of a mouthpiece 302. It would alternatively be possible for the device to be adapted for nasal use instead of oral use, in which case a nasal outlet would replace the mouthpiece. The same is true of the other embodiments described herein. The outlet end of the mouthpiece is closed by a cap 304 which is pivotally mounted on the body by means of a pivot 306 for pivotal movement with respect thereto. The powder containers are held in two stacks within a cartridge 307. Initially, all the containers are in a stack 308, which consists of a number of unused (i.e. full) containers surmounted by one empty container which acts as an initial lid to dose off the top of the stack. The "top" for this purpose is the end of the stack nearer the mouthpiece 302. A stack of used (i.e. empty) containers is formed during operation of the device in the chamber indicated by reference numeral 310. A window 311 is provided in the body 300, through which the stack of empty containers can be viewed when there are sufficient containers therein to fill the chamber 310 almost completely. This gives warning to the user when the full containers have almost all been used.

Figure 9A:
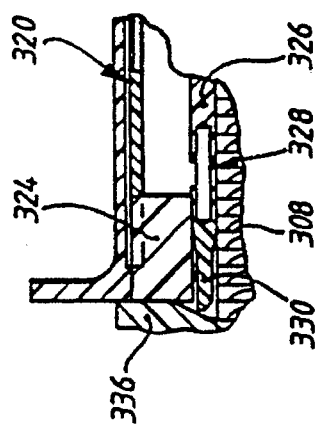
FIG. 9a shows a cut-away detail at the top of the stack of containers of the embodiment of FIG. 9.

The end of the stack 308 remote from the mouthpiece 302 is seated on a spring member 312 which comprises a top member 314, a base member 316 and a compression spring 318 which urges the members 314 and 316 away from one another. One end of a U-shaped pusher member 320 bears against the base member 316. The pusher member 320 passes round a guide surface 322, over which it can slide, and the other end thereof bears against a pad 324 which can be seen in FIG. 9a and which is slidable in the chamber 310. The pusher 320 is in the form of a flexible plate, for example of a plastics material. The guide surface 322 is formed on one end of a rod 326, the other end of which, as can be seen in FIG. 9a, provides a surface against which one end of a compression spring 328 can bear. The other end of the spring 328 bears against the end of a blade 330, the purpose of which is described below.

The shaft 306, which provides pivotal movement between the cap 304 and the body 300, carries a crank arm 332. Preferably, there is a pair of crank arms, one at each end of the shaft 306, only one of these arms being visible in FIG. 9. The crank arm 302 and shaft 306 rotate with the cap 304, and thus with respect to the body 300.

Figure 9:
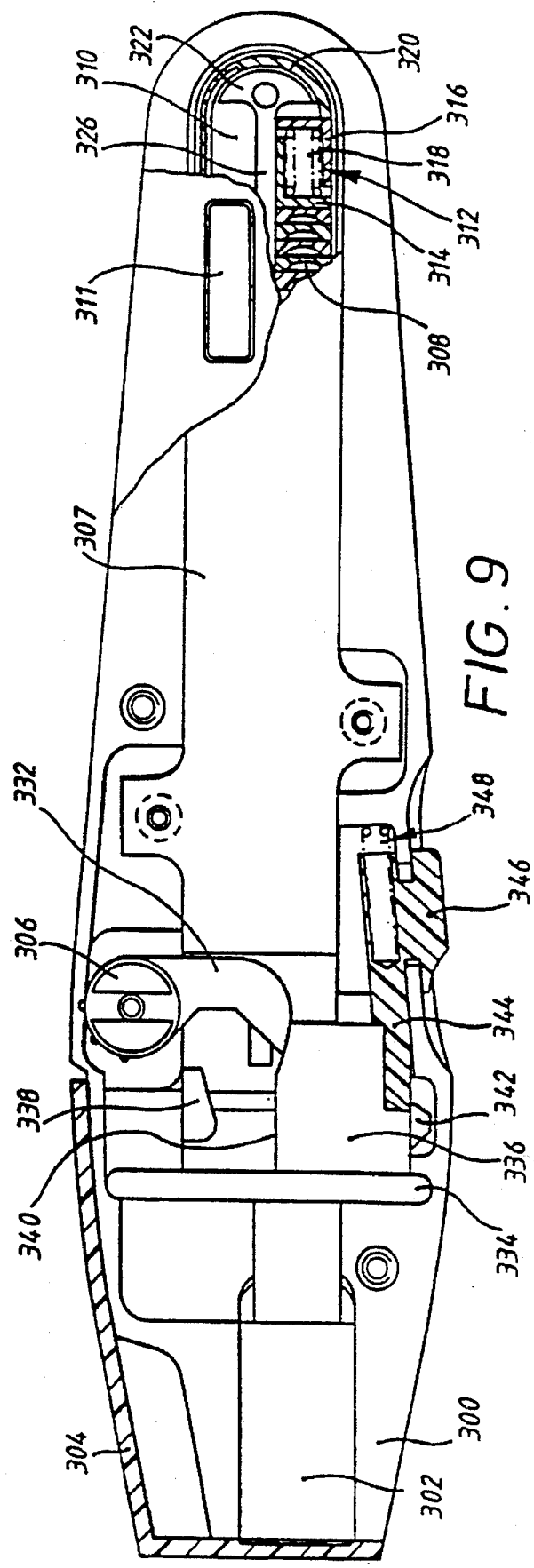
FIG. 9 is a longitudinal section, with portions cut away, showing a further embodiment.

Beneath the inner end of the mouthpiece 302, which is defined by a plate 334, there is mounted a slider 336 which is movable transversely with respect to the longitudinal axis of the mouthpiece 302, i.e. in a direction which is upward and downward as viewed in FIG. 9. The slider has a lug 338 which is engaged by the end of the crank arm 332 after the arm has rotated clockwise from its illustrated position through an angle of about 45°. If a second crank arm 332 is provided there is a corresponding second lug 338 for it to engage. The slider also defines a bearing surface 340 with which a curved surface on the crank arm 332 can engage. The purpose of this is described below in connection with the operation of the device. It can further be seen in FIG. 9 that the slider has a bead 342 on one end thereof. The end of a safety catch 344 operable by a button 346 engages behind the bead 342, and is urged into the engaging position by a compression spring 348. So long as the catch 344 engages behind the bead 342 the slider 336 cannot move.

As already mentioned, at the start there is a complete stack 308 consisting entirely of unused containers except for that nearest the mouthpiece. The chamber 310 is empty. To use the device the user exerts a force on the button 346 to urge the catch out of engagement behind the bead 342, against the force of the spring 348. While still holding the button in that position the user pivots the cap 304 to uncover the mouthpiece 302. The first 45° of this pivotal movement has no effect on the operation of the device, thus allowing for example the sort of movement which might be made by someone, particularly a child, playing with it, without actually moving the slider. Further angular movement beyond the initial 45° causes the crank arm 332 to engage the lug 338 and, provided the safety catch 344 is still out of engagement with the bead 342, the slider 336 is caused to move laterally. The resistance of the device to accidental operation is enhanced by the fact that lateral movement cannot take place, however, unless the user is at that point in time holding down the button 346.

Figure 10A:
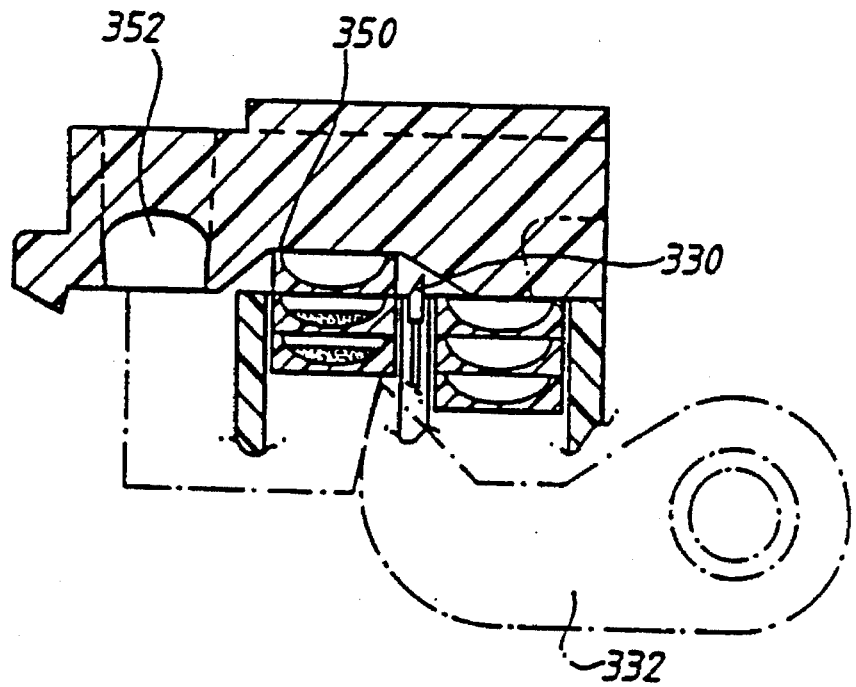
FIGS. 10a and 10b show, diagrammatically and in section, the upper portion of the embodiment of FIGS. 9 and 9a in its inoperative and operative positions, respectively.
Figure 10B:
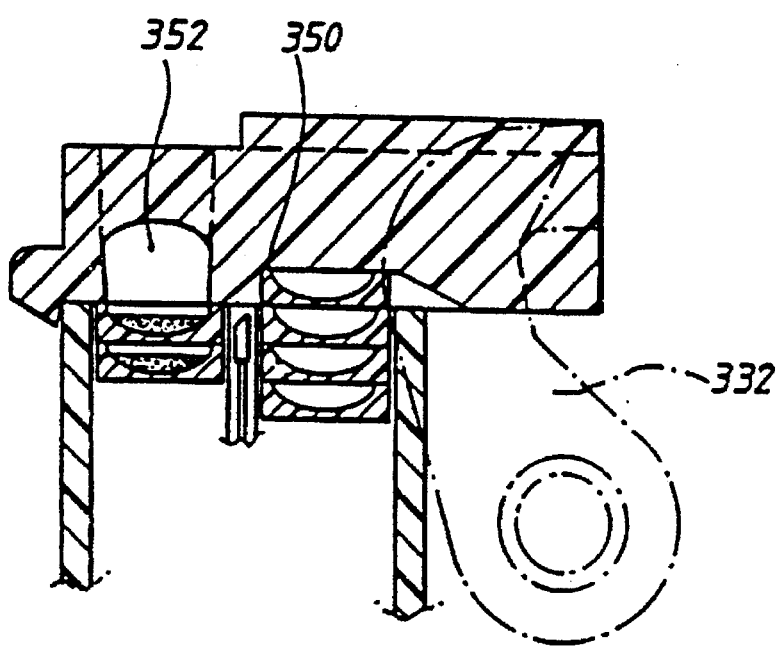

At the start of this movement the empty container at the top of the stack 308 is in a recess 350 on the underside of the slider 336 (see FIG. 10a). The lateral movement of the slider 336 transfers the empty container at the top of the stack 308 past the blade 330, which is depressed against the force of the spring 328, so that the empty container is on the end of the pad 324. The pad is thereby depressed, and movement of the pad is transmitted by the pusher 320 to the spring member 312. At this point the spring top member 314 cannot move any further, so the result is that the compression spring 316 is compressed by an amount equal to the thickness of one container. The empty container which is now bearing against the pad 324 forms the start of the stack of used containers.

Figure 11:
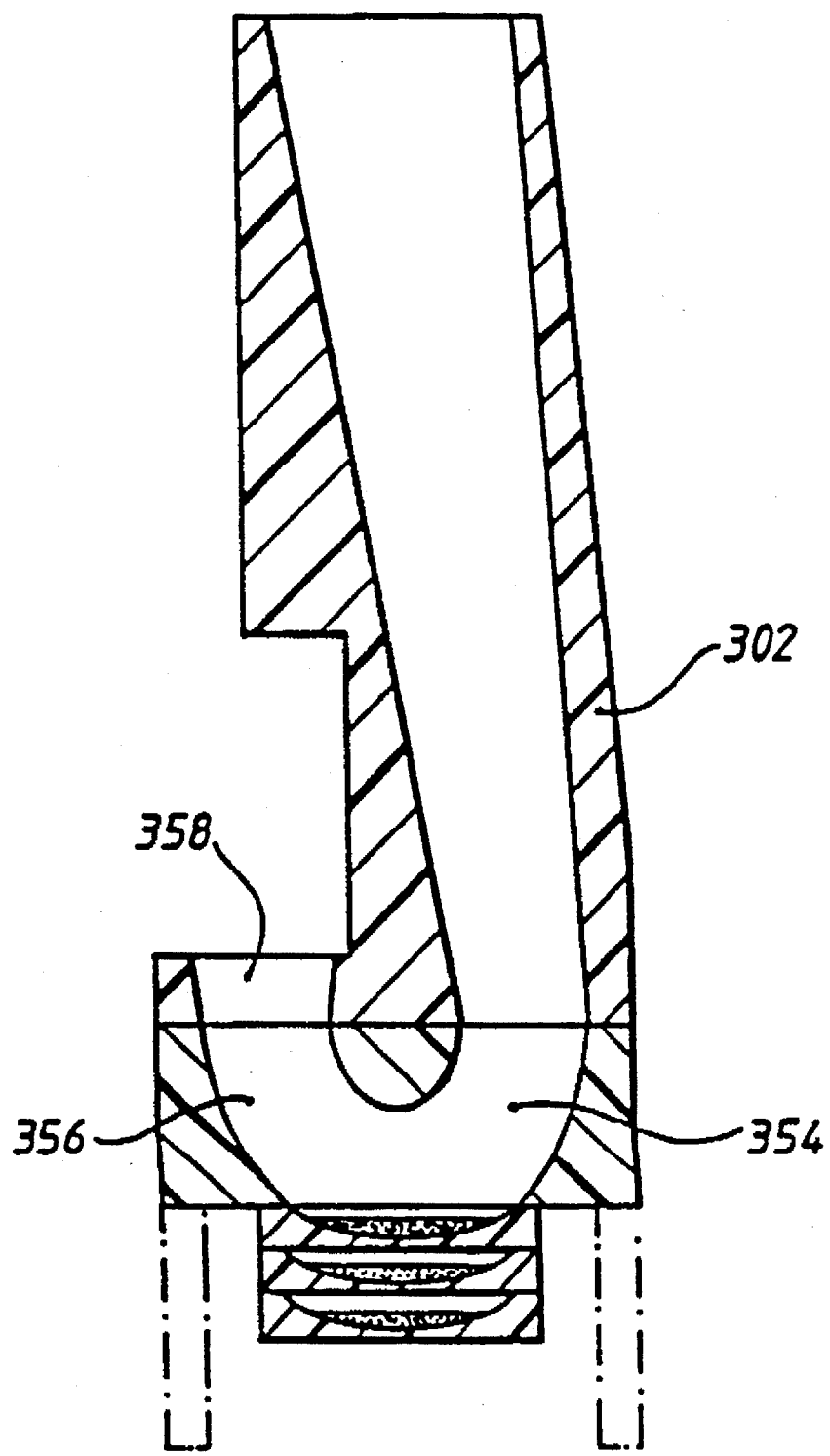
FIG. 11 is a section through the stack of unused containers shown in FIG. 10b, taken at right angles thereto, along with a mouthpiece.
Figure 12:
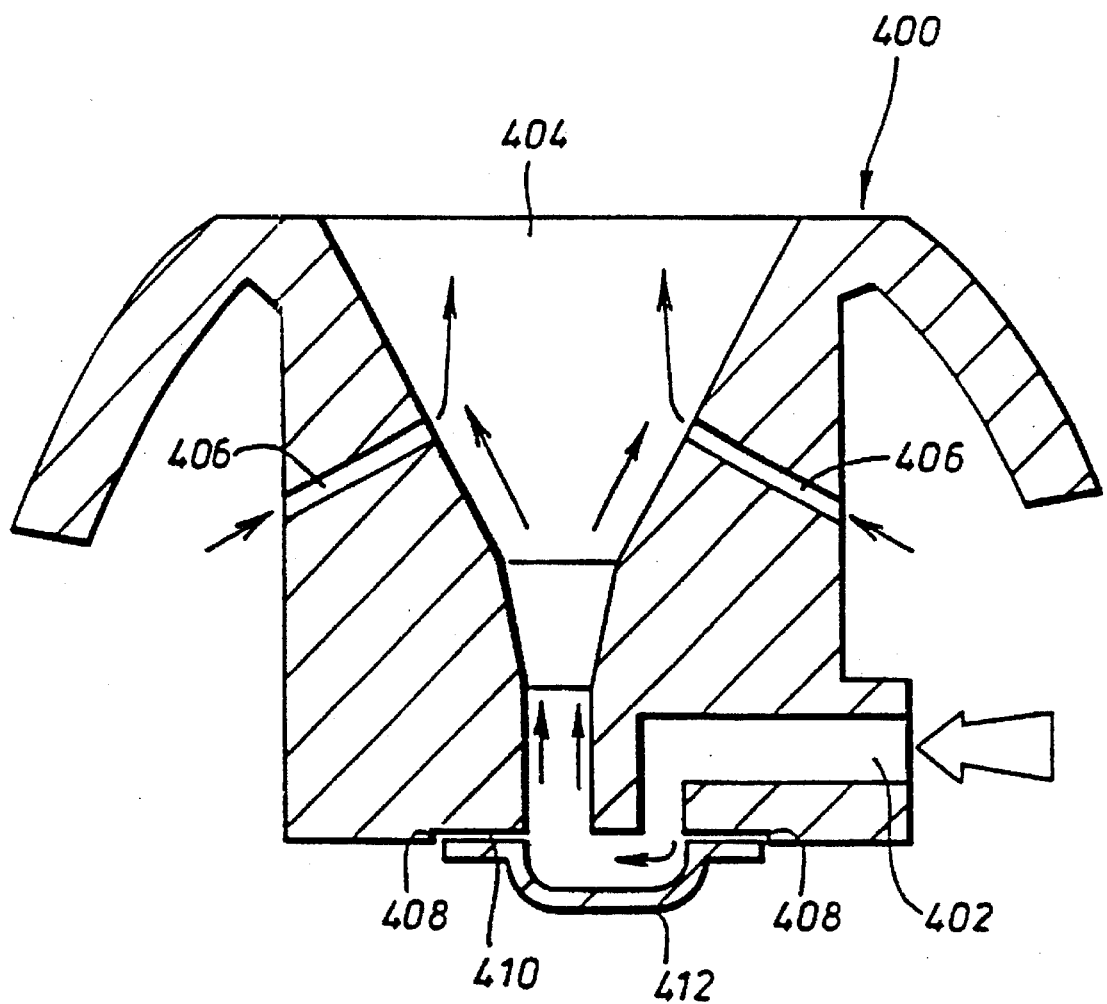
FIG. 12 is a schematic longitudinal section through another embodiment.

The above described movement of the empty container brings a full container into alignment with an opening 352 in the underside of the slider. A pair of passages 354, 356 with which the opening 352 communicates are in alignment respectively with an aperture which communicates with the interior of the mouthpiece 302 and an aperture 358 in the plate 334 through which air can enter from the exterior of the device 336 (see FIG. 11). Accordingly, when the user now inhales through the mouthpiece, air flows in through the aperture 358 and passage 356, entrains powder from the container, and flows out through the passage 354 into the mouthpiece and thence to the patient. As can be seen in FIG. 11, the aperture 358, the passages 354 and 356, and the interior of the mouthpiece 302, define, together with the depression in the uppermost powder container, a structure which constitutes a venturi.

When the cap 304 is rotated back to its closed position, the curved surface on the rear of the crank arm 332 engages the surface 340 on the slider 336, and forces the slider back to its original position. During this movement the blade 330 prevents the empty container from moving back to the top of the stack 308. The device is now ready for the user to repeat the operation just described. The embodiments just described are devices which are intended to be thrown away after all the containers have been used. Alternatively, however, the device could comprise a replaceable cartridge having the stacks of unused and used containers therein, with the cartridge being replaced once all the containers had been used. The cartridge could include all or part of a slider mechanism for transferring containers from one stack to the other.

FIG. 12 shows part of a device comprising a mouthpiece 400 having a main air inlet, passage 402, an air outlet passage 404, and auxiliary air inlets 406 which communicate with the air outlet passage intermediate its ends. The inlet passage 404 diverges as viewed from its upstream end to its downstream end. The mouthpiece has a pair of shoulders 408 formed therein which define the sides of a track 410, the track running perpendicular to the plane of the paper in FIG. 12.

The device is intended to handle a medicament pack in which a plurality of powder containers are defined between an elongate base sheet formed with longitudinally spaced blisters and a cover sheet hermetically sealed thereto. FIG. 12 shows one of the blisters, labelled 412 ready for use, with the portion of the base sheet (not shown) which would normally cover it, peeled away. The blister is positioned so that one edge region is opposite the downstream end of the main air inlet passage 402 and the opposite edge region is opposite the upstream end of the air outlet passage 404. The main air inlet passage, the interior of the blister, and the air outlet passage form between them what is, in effect a venturi. When the user inhales through the mouthpiece, the air flow through the venturi efficiently entrains the powder which is in the blister. Air entering through the auxiliary air inlet 406 ensures that the resistance to flow experienced by the user is not unacceptably high. To bring the next blister into position for use, the medicament pack is pulled along the track 410.

I claim:

1. An inhalation device for use in inhaling material in powder form comprising:

means for holding a powder container having a powder containing depression at a use station within said inhalation device; and inhalation means for enabling the powder to be inhaled from the powder container at the use station, said inhalation means comprising an outlet communicating with the powder container by a passage, said passage including wall means leading smoothly into said depression wherein said wall means and said depression collectively complete a curved section of said passage to define a venturi.

2. A device according to claim 1, further comprising means for storing at least one unused powder container and means for feeding said at least one unused powder container to the use station.

3. A device according to claim 2, further comprising means for retaining a stack of used powder containers, and means for delivering each used powder container from the use station after the powder has been inhaled therefrom to said retaining means.

4. A device for use in inhaling material in powder form comprising:

a body portion, at least one container located in said body portion, said at least one container including a depression adapted to contain powder to be inhaled;

a member attached to said body portion and defining an inhalation outlet through which powder contained in the depression of said at least one container is adapted to be inhaled, said inhalation outlet being in fluid communication with an inhalation passage leading from the inhalation outlet to said at least one container, said inhalation passage leading smoothly into the depression such that the depression completes a curved section of the inhalation passage at which a venturi is formed.

5. The device according to claim 4, including a plurality of containers wherein said body portion comprises a first storage chamber for housing unused powder containers and a second storage chamber for housing used powder containers.

6. The device according to claim 5, wherein said first and second chambers are interconnected and defined by a generally U-shaped passage formed in said body portion.

7. The device according to claim 6, further comprising means, located in said first and second chambers, for biasing both the unused and used powder containers toward said member.

8. The device according to claim 7, wherein said biasing means consists of a coil spring.

9. The device according to claim 5, wherein said member is movable between a first position wherein said inhalation passage opens into said first storage chamber and a second position wherein said inhalation passage is closed off from said first storage chamber.

10. The device according to claim 9, wherein said member further comprises means for transferring said at least one container from said first storage chamber to said second storage chamber as said member is moved between said first and second storage positions.

11. The device according to claim 10, wherein said member is slidably attached to said body portion for movement between said first and second positions.

12. The device according to claim 10, wherein said member is rotatably attached to said body portion for movement between said first and second positions.

13. The device according to claim 4, further comprising a cap attached to said body for movement between a first position wherein said inhalation outlet is covered by said cap and a second position wherein said inhalation outlet is exposed.

* * * * *